(12) United States Patent
King et al.

(10) Patent No.: US 10,995,275 B2
(45) Date of Patent: May 4, 2021

(54) HYDROTROPIC COMPOSITION AND ITS USES

(71) Applicant: Kemira Oyj, Helsinki (FI)

(72) Inventors: Alistair King, Helsinki (FI); Evangelos Sklavounos, Helsinki (FI); Tiina Laaksonen, Helsinki (FI); Antti Rantamäki, Vantaa (FI); Susanne Wiedmer, Kauniainen (FI); Lasse Kyllönen, Espoo (FI); Suvi-Katriina Ruokonen, Helsinki (FI)

(73) Assignee: Kemira Oyj, Helsinki (FI)

( * ) Notice: Subject to any disclaimer, the term of this patent is extended or adjusted under 35 U.S.C. 154(b) by 0 days.

(21) Appl. No.: 16/472,914

(22) PCT Filed: Jan. 11, 2018

(86) PCT No.: PCT/FI2018/050015
§ 371 (c)(1),
(2) Date: Jun. 24, 2019

(87) PCT Pub. No.: WO2018/130748
PCT Pub. Date: Jul. 19, 2018

(65) Prior Publication Data
US 2019/0345392 A1 Nov. 14, 2019

Related U.S. Application Data

(60) Provisional application No. 62/444,864, filed on Jan. 11, 2017.

(51) Int. Cl.
*C10G 1/04* (2006.01)

(52) U.S. Cl.
CPC .................................. *C10G 1/045* (2013.01)

(58) Field of Classification Search
None
See application file for complete search history.

(56) References Cited

U.S. PATENT DOCUMENTS

| | | |
|---|---|---|
| 3,854,531 A | 12/1974 | Carlin |
| 4,388,170 A | 6/1983 | Schmid et al. |
| 4,452,692 A | 6/1984 | Kneissl et al. |
| 2008/0039345 A1 | 2/2008 | Kippie et al. |
| 2016/0244606 A1 | 8/2016 | Ravichandran et al. |

FOREIGN PATENT DOCUMENTS

| | | |
|---|---|---|
| WO | 2016107388 A1 | 7/2016 |
| WO | 2016198747 A1 | 12/2016 |

*Primary Examiner* — Tam M Nguyen
(74) *Attorney, Agent, or Firm* — Robin L. Teskin; Baker, Donelson, Bearman, Caldwell & Berkowitz PC

(57) ABSTRACT

A hydrotropic composition including at least one surface active cationic component, which is selected from a group of cholinium, guadinium or tetramethylguadinium, preferably cholinium, and a straight or branched carboxylate anion having at least six carbon atoms and its uses, for treating of oil sands or the like, for treating tailings from separation of bitumen, asphaltenes or the like.

11 Claims, 11 Drawing Sheets

Choline     Neodecanoate    R + R' + R" = C8

Guanidine     Decanoate

Tetramethylguanidine     
Isostearate

HYDROTROPIC COMPOSITION AND ITS USES

PRIORITY

This application is a U.S national application of the international application number PCT/FI2018/050015 filed on Jan. 11, 2018 and claiming priority of provisional application 62/444,864 filed on Jan. 11, 2017 the contents of all of which are incorporated herein by reference.

The present invention relates to a hydrotropic composition and its uses according to the preambles of the enclosed independent claims.

Ionic liquids (ILs) are organic salts that are typically in the molten state at temperatures below 100° C. ILs have been considered as "green" alternatives for molecular solvents, since there is lower risk of environmental release, through the atmosphere, due to their low vapor pressures. However, due to their water solubility, ILs may be potent ecotoxicological hazards particularly for the organisms inhabiting aquatic environments. The risks for the environment exist throughout the whole life cycle of the ILs, from synthesis to application and from application to disposal.

The applications of the ILs are as diverse as their structures and the potential new anion-cation pairs are practically limitless. Surface active ILs, in which either the cation or anion have one or several alkyl chains, have been used in numerous applications, such as, extraction of organic compounds, metal ions and radioactive isotopes, as templates in production of porous materials, in microemulsions and as demulsifiers in petroleum chemistry.

When developing novel ILs for industrial applications, their toxicological effect is of importance due to the environmental responsibilities determined by legislation, such as, the European Union regulation regarding registration, evaluation, authorization, and restriction of chemicals (REACH). Also, investigation of the IL structural properties and the toxicity mechanisms can provide useful information for development of ILs that are efficient in their application, but less harmful for the environment.

An object of this invention is to minimise or even totally eliminate the disadvantages existing in the prior art.

The invention is defined in the characterising parts of the enclosed independent claims. Some preferable embodiments of the invention are defined in the dependent claims. All described features apply both for the use as well as the composition of the invention, whenever applicable, even if it not necessarily stated so.

Typical hydrotropic composition according to the invention comprises
- at least one surface active cationic component, which is selected from a group of cholinium, guadinium or tetramethylguadinium, preferably cholinium, and
- a straight or branched carboxylate anion having at least six carbon atoms.

Now it has been surprisingly found out that the hydrotropic composition according to the present invention shows low toxicity in aqueous environment. In the present study novel surface-active cholinium (Ch), guanidinium (GND), and tetramethylguanidinium (TMG) based ILs, in combination with isostearate, decanoate and neodecanoate anions, were investigated (FIG. 1 and Table 1). The ILs were developed as more advanced or low toxicity structures for enhanced extraction processes, to be used in biomass or petroleum chemistry and the cation and anion pairs were selected from this application point of view.

The surface active cationic component of the hydrotropic composition originates from an organic salt which is in molten state at temperatures below 100° C. This means that it is an ionic liquid.

According to one embodiment of the invention the carboxylate anion of the hydrotropic composition has 6 to 20 carbon atoms, preferably from 10 to 18 carbon atoms. The carboxylate anion may be branched or unbranched, preferably branched. According to one preferred embodiment the carboxylate anion is isostearate, decanoate or neodecanoate, preferably neodecanoate.

According to one embodiment the carboxylate anion may be isostearate, which is derived by tall-oil fatty acid dimerization and hydrogenation of a monomeric residue.

According to another embodiment the carboxylate anion may be isostearate, which is derived by tall-oil fatty acid trimerization and hydrogenation of a monomeric residue.

According to another embodiment the carboxylate anion may be neodecanoate, which is obtained through Reppe-Koch chemistry of acid-catalysed hydrocarboxylation on octene isomers, derived from propene polymerisation.

In this study we investigated the acute cytotoxicities of seven of the aforementioned ILs in aquatic environment. The toxicity of the cation is commonly known to increase as the function of the alkyl chain length. There are fewer studies investigating the effect of the alkyl chains in IL anions and particularly the impact of the carboxylate ILs. However, based on these studies the elongation of the carboxylate alkyl chain increases the toxic effect in similar fashion than to cations. Hence, due to the long-chain carboxylates the ILs in the present study were assumed to be surface active and the nature of these anions were expected to determine the toxicities of the ILs. In contrast, the cations were expected to have a less significant role due to their low chain-length. The effect of the cations on the behavior of the ILs was investigated by testing also the toxicities of the equivalent isostearate, decanoate, and neodecanoate sodium salts, as reference materials. Isostearate and neodecanoate anions are derived from technical formulations of isostearic acid and neodecanoic acid. Both are branched acids. Isostearic acid is bio-based, derived from tall-oil fatty acid di/trimerization and hydrogenation of the monomeric residue. Neodecanoic acid is a low-cost petrochemical-based derivative, obtained through Reppe-Koch chemistry (acid-catalysed hydrocarboxylation) on octene isomers, derived from propene polymerisation.

The toxicities were determined by exposing *Vibrio fischeri* marine bacteria to aqueous solutions of ILs in differing concentrations. These bacteria have successfully been used for IL toxicity assessments in a myriad of studies. A recent comparison was performed between *V. fischeri* and three other standardized toxicity assays utilizing aquatic organisms, namely *Daphnia magna* (a fresh water crustacean), *Selenastrum capricornutum* (a freshwater algae) and *Phaeodactylum tricornutum* (a seawater algae). Based on this study, *V. fischeri* was the most sensitive for the surface-active toxicants (detergents) and, therefore, these bacteria were selected for the toxicity assessment of surface-active ILs in the present study.

The median effective concentrations ($EC_{50}$) were determined for each IL. Since the toxic effect was thought to be caused by permeation of these surface-active molecules into the cell wall of the bacteria, related interactions of ILs with biomimetic liposomes were investigated utilizing differential scanning calorimetry (DSC). In DSC experiments, dipalmitoyl phosphatidylcholine (DPPC) liposomes were used as biomimicking membranes and the change in the main phase transition temperature ($T_m$) of the DPPC bilayer was followed, as a function of the IL concentrations. Such measurements could potentially offer more information on how the aforementioned ILs interact with the lipid bilayers. Lastly, the critical micelle concentrations (CMC) were defined for the ILs. Based on the CMCs, it can be defined if the ILs are dissolved as singly dispersed molecules or form a dispersion of spherical micelles, or other self-assembled structures (aggregates). Therefore, it can be determined if the interactions with the bacteria or liposomes take place between IL aggregates or singly dispersed IL molecules.

Our results demonstrate that the long chain carboxylate anions define the toxicities of these ILs, whereas the non-surface-active cations have less impact on the toxicity. In addition, based on the DSC studies, the anion alkyl chain length and branching mainly define the extent of the interactions. However, in contrast to the toxicity studies, the anion impact is more affected by the accompanying cation.

According to one embodiment of the invention the composition has a median effective concentration $EC_{50}$ value >10 mg/l, preferably >100 mg/l, measured using *Vibrio fischeri* bacteria. For example, the composition which comprises decanoate or isostearate as carboxylate anion, may have a median effective concentration $EC_{50}$ value 10-200 mg/l. Alternatively, the composition may comprise neodecanoate as carboxylate anion and have a median effective concentration $EC_{50}$ value 100-1000 mg/l.

According to one embodiment of the invention the composition has an average critical micelle concentration CMC>10 mM, preferably >100 mM.

In the present context the term surfactant is understood as a substance that in the absence of any other solute form organised phases, such as micelles or other similar type of closed aggregates, with an increase in concentration. In the present context the term hydrotrope is understood as a substance, which only form structured phases when there is a co-solvent, usually hydrophobic and poorly soluble otherwise, present in the mixture. Thus, hydrotropes can be used to increase the solubility of typically insoluble materials.

In the present context the term carboxylate denotes a salt or ester of a carboxylic acid, such as fatty acid.

The composition according to the invention may be used for treating of oil sands or the like. Further, the composition according to the invention may be used for treating tailings from separation of bitumen, asphaltenes or the like. Oil sands, which are also known as tar sands, are mixtures of clay, sand, water, and heavy hydrocarbons, such as bitumen. They provide a potential source of hydrocarbons for petrochemical industry. The present invention provides an effective composition for treating oil sands or tailings, especially oil sand tailings.

According to one embodiment of the invention the composition has hydrotropic properties between 20/80 to 90/10% (w/v), given as ratio of composition to water.

LIST OF FIGURES

Figures 4A, 4B, 4C:
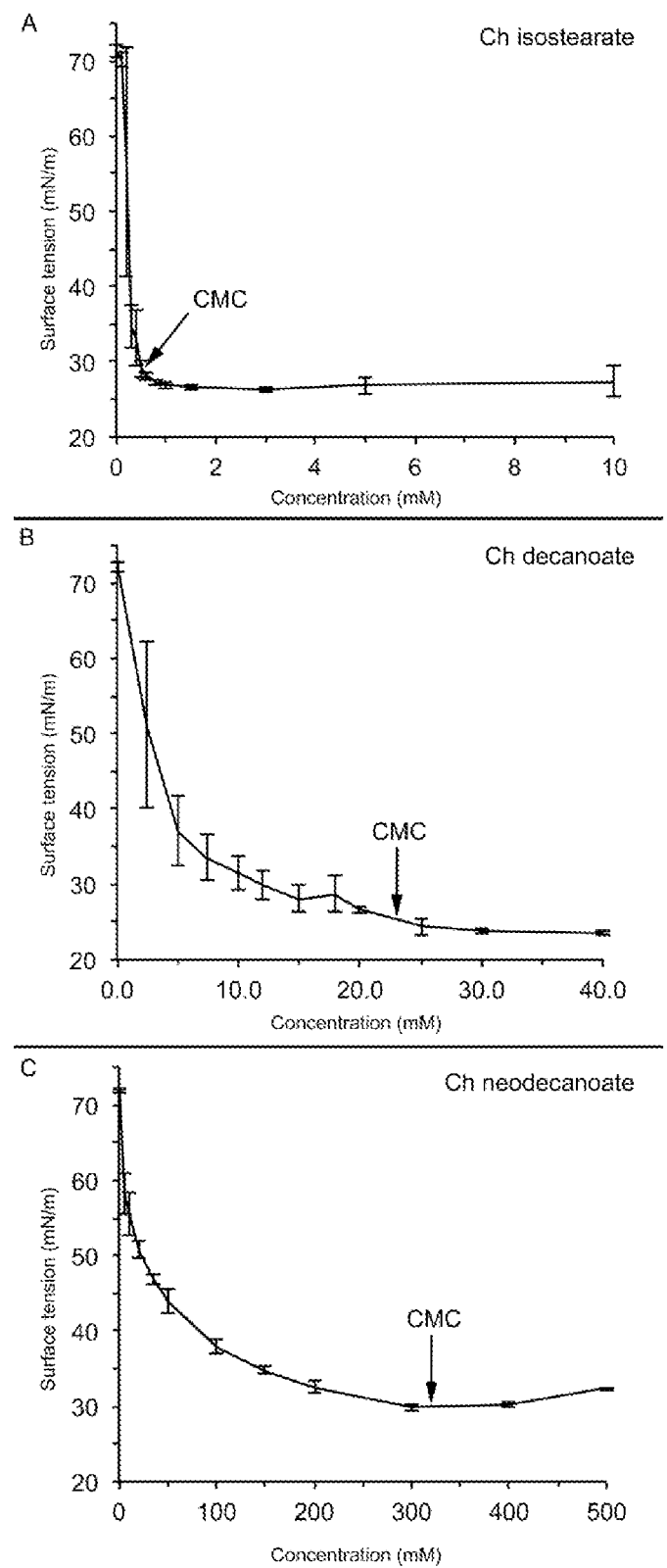

FIGS. 4A, 4B and 4C show CMC curves for Ch isostearate, Ch decanoate and Ch neodecanoate exemplifying the differing surfactant properties of each IL. The surface tension data obtained using the pendant drop method was plotted as a function of the IL concentrations. The exact CMCs were defined by logarithmic fitting.

Figure 5A:
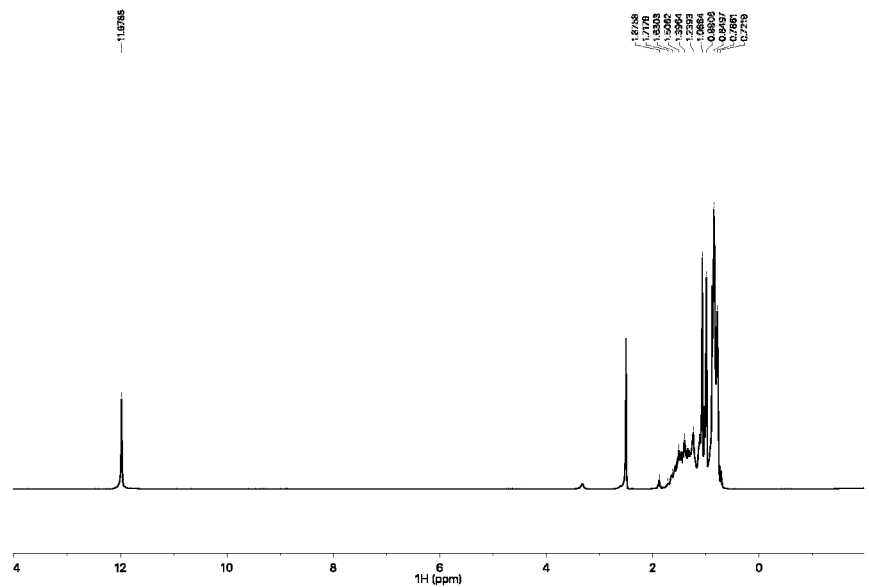
Figure 5B:
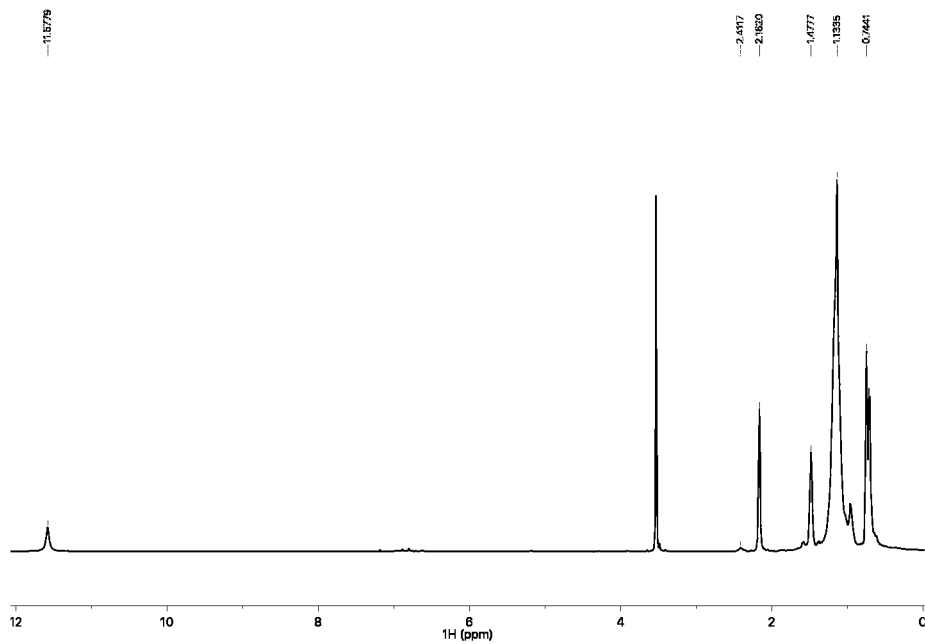
Figure 5C:
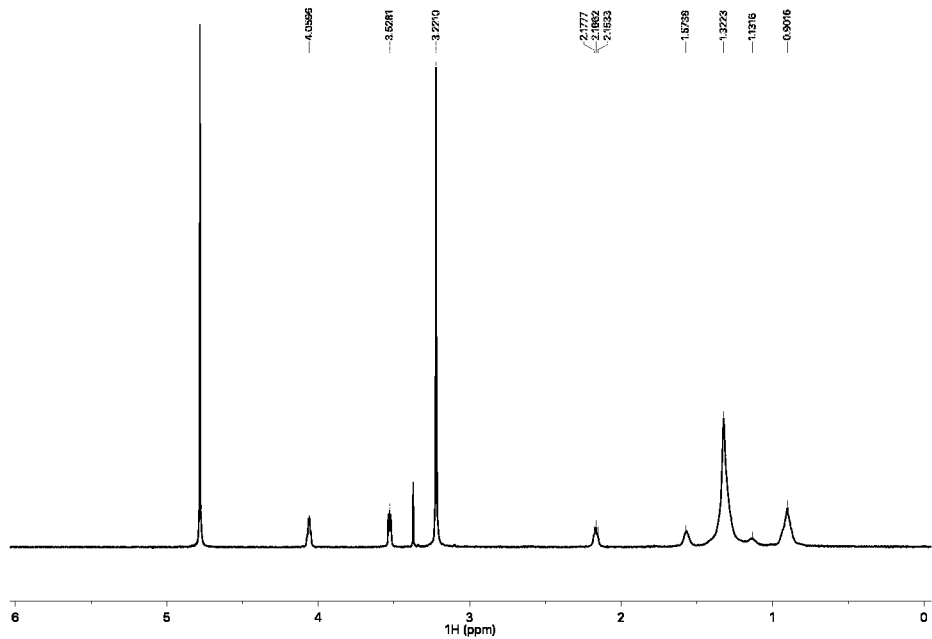
Figure 5D:
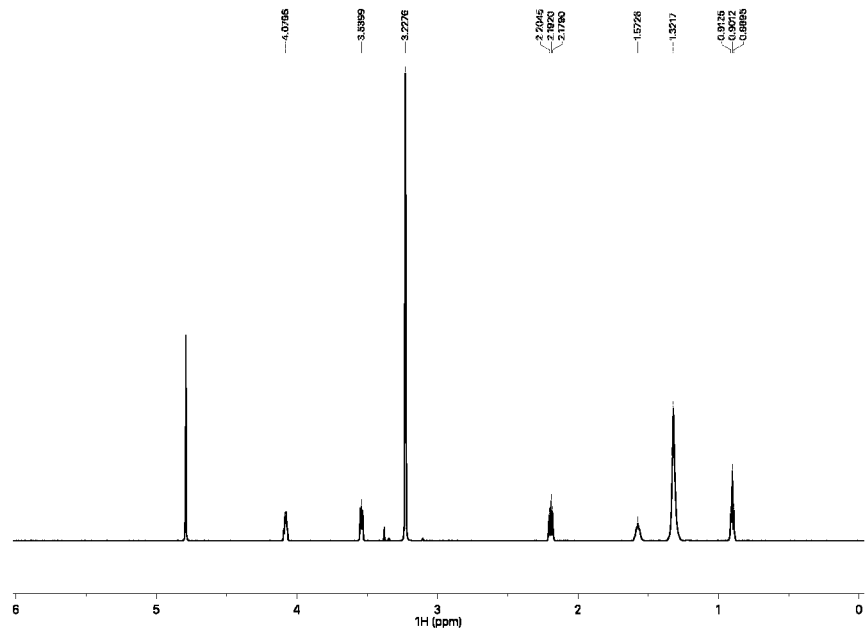
Figure 5E:
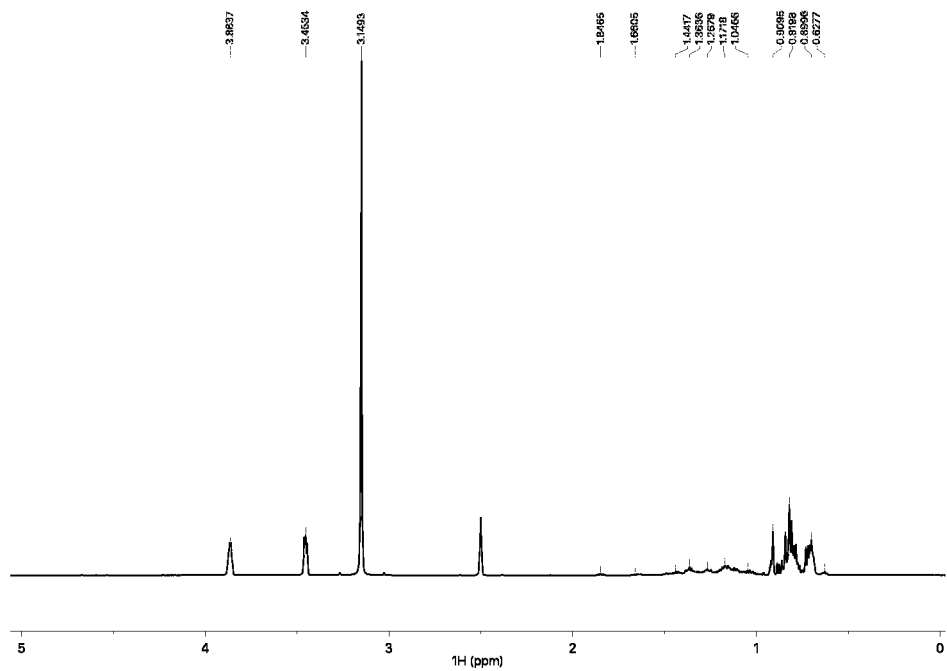
Figure 5F:
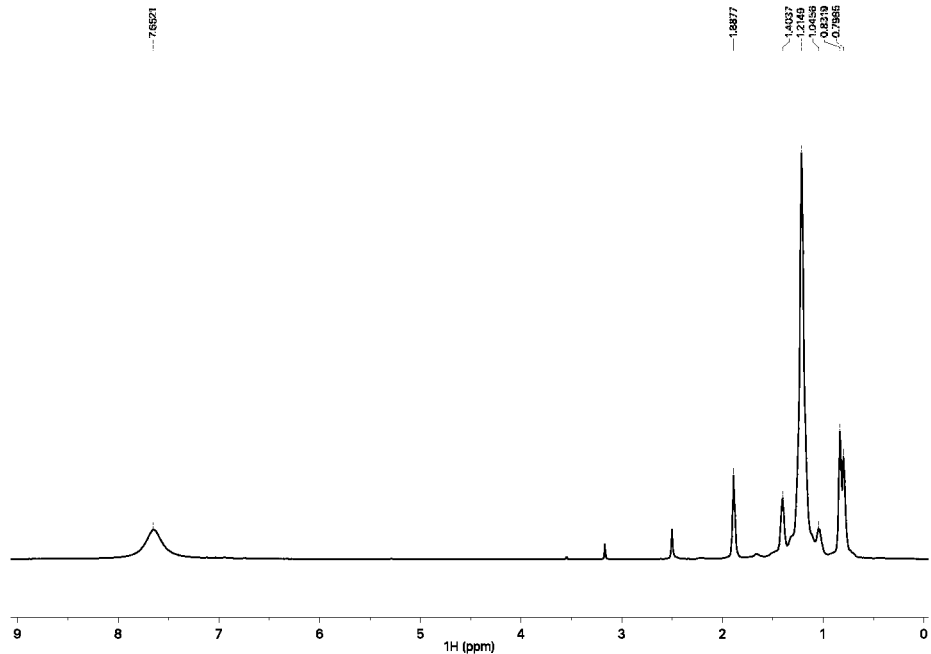
Figure 5G:
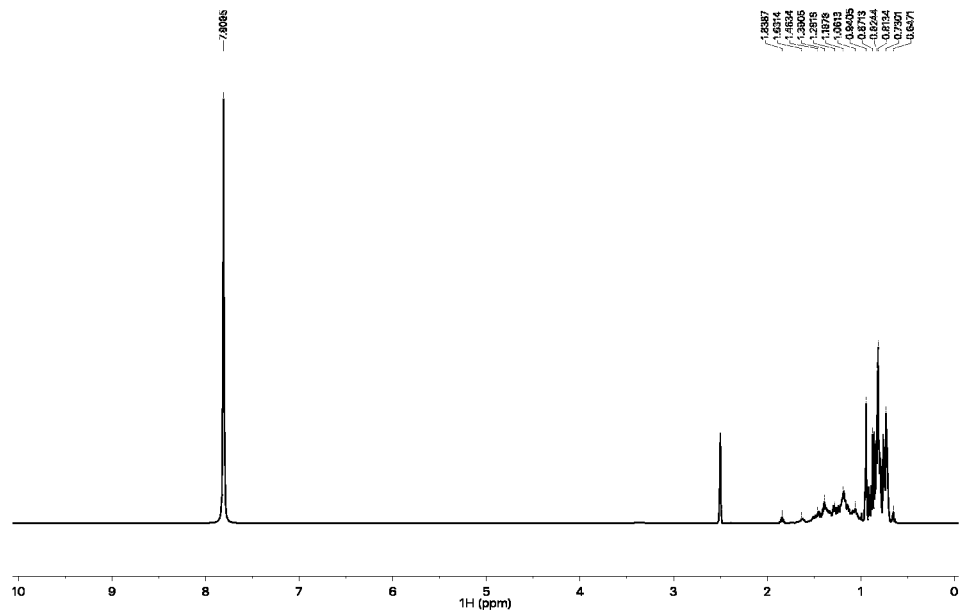
Figure 5H:
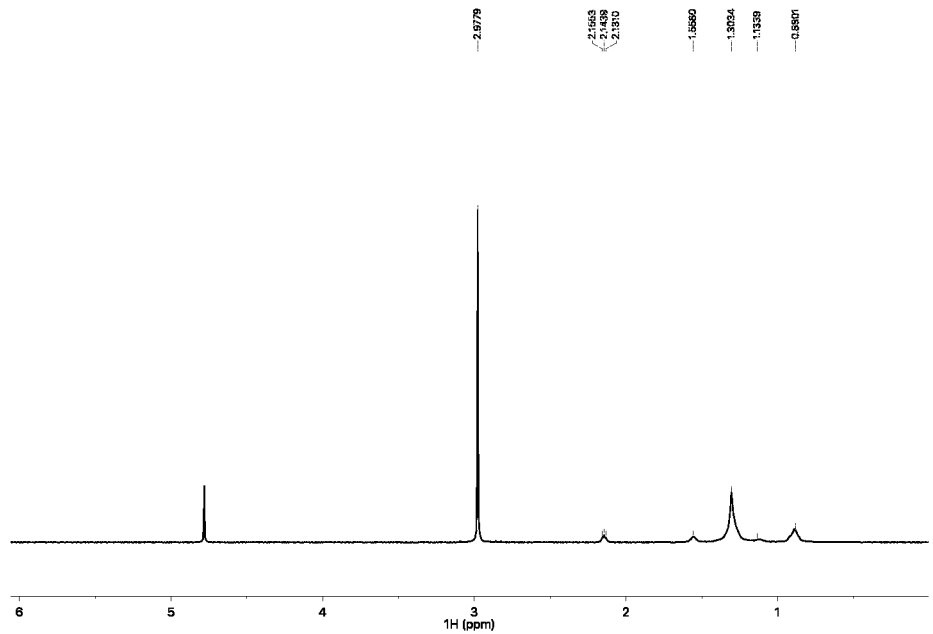
Figure 5I:
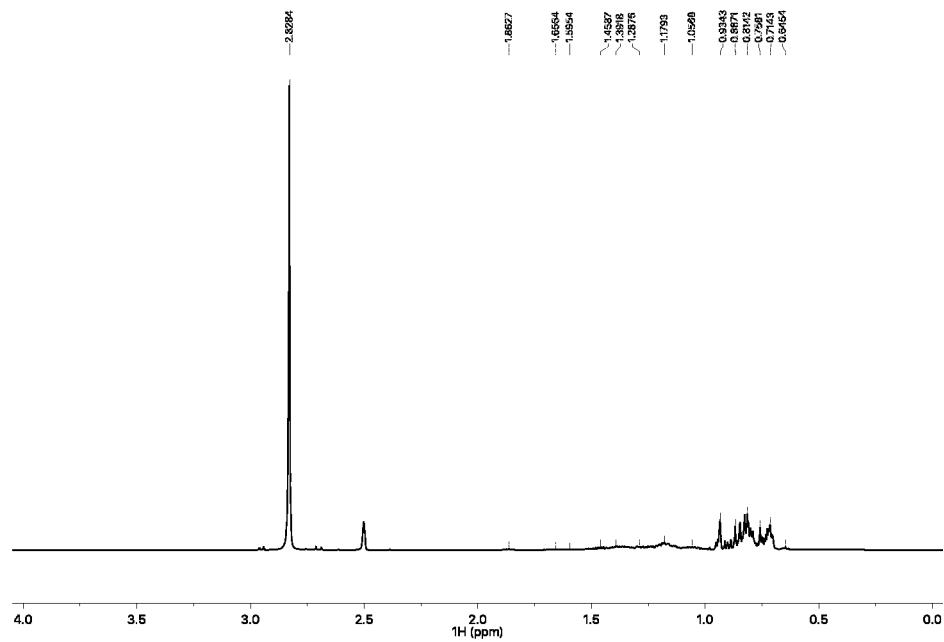
Figure 5J:
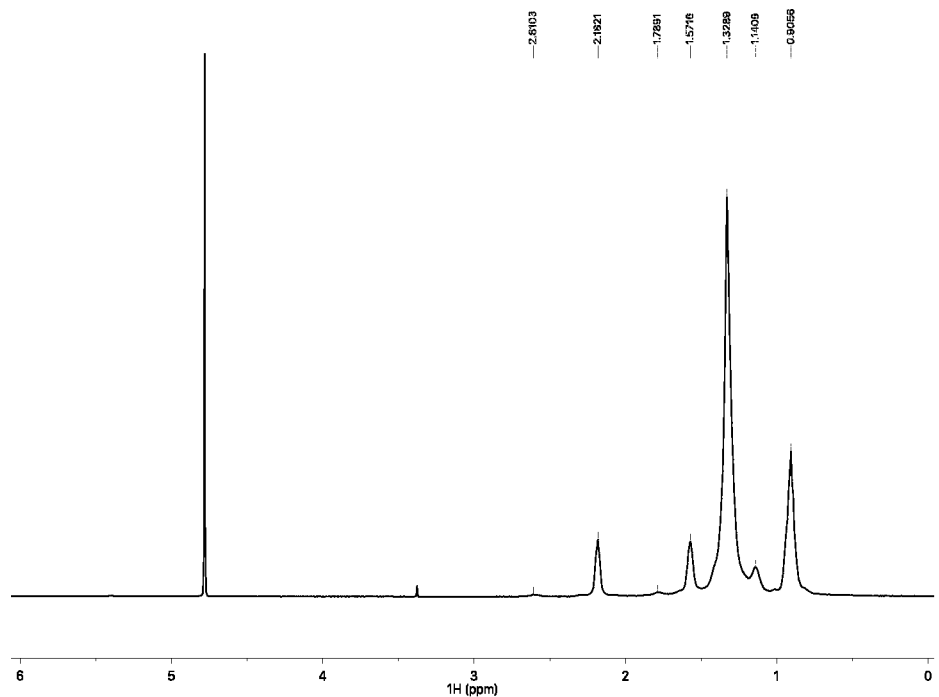
Figure 5K:
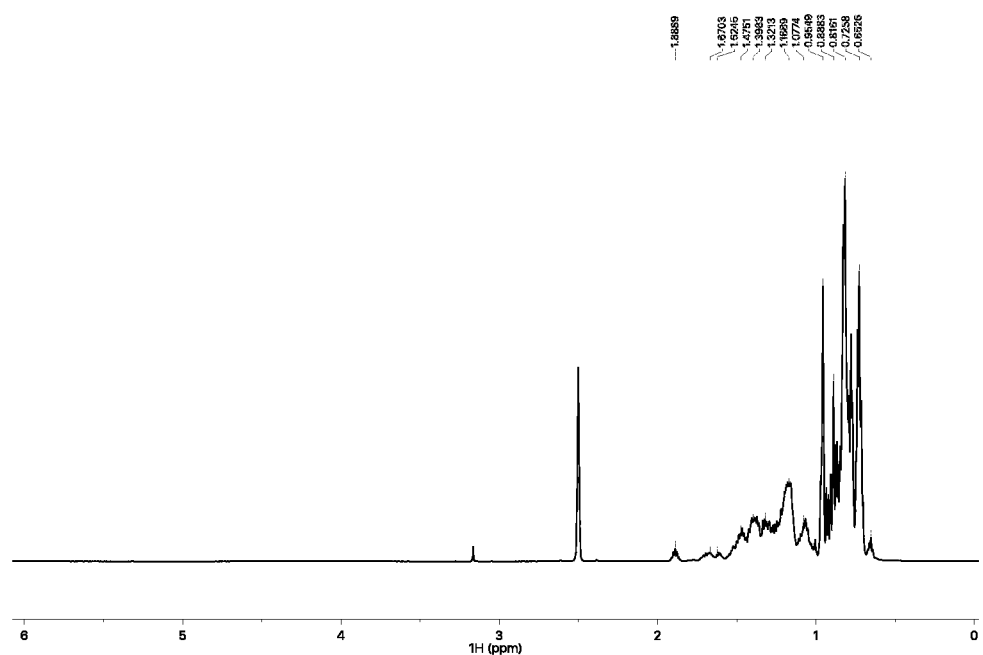

FIGS. 5A-5K show $^1$HNMR spectra (600 MHz) of synthesized ionic liquids. FIG. 5A shows $^1$HNMR spectra of neodecanoic acid—Versatic™ acid (DMSO-$d_6$); FIG. 5B shows $^1$HNMR spectra of isostearic acid—Pristorine™ 3501 (DMSO-$d_6$, with 1,4-dioxane as internal standard); FIG. 5C shows $^1$HNMR spectra of choline isostearate ($D_2O$); FIG. 5D shows $^1$HNMR spectra of choline decanoate ($D_2O$); FIG. 5E shows $^1$HNMR spectra of choline neodecanoate (DMSO-$d_6$); FIG. 5F shows $^1$HNMR spectra of guanidinium isostearate (DMSO-$d_6$); FIG. 5G shows $^1$HNMR spectra of guanidinium neodecanoate (DMSO-$d_6$); FIG. 5H shows $^1$HNMR spectra of 1,1,3,3-tetramethylguanidinium isostearate ($D_2O$); FIG. 5I shows $^1$HNMR spectra of 1,1,3,3-tetramethylguanidinium neodecanoate (DMSO-$d_6$); FIG. 5J shows $^1$HNMR spectra of sodium isostearate ($D_2O$); and FIG. 5K shows $^1$HNMR spectra of sodium neodecanoate (DMSO-$d_6$).

ACUTE CYTOTOXICITY

The toxicity measurements were performed from an ecotoxicological point of view, since ILs are potentially hazardous for the environment and particularly for organisms in aquatic environments. Therefore, *V. fischeri* marine bacteria were utilized in these measurements. $EC_{50}$ values were determined for seven water-soluble surface-active ILs. The ILs in this study included Ch-, GND-, TMG-based ILs with straight and branched (iso and neo forms) fatty acid chains, namely isostearates, decanotes and neodecanoates. As a reference, the toxicities of the sodium salts of these carboxylates were measured in order to obtain information on the effect of the cation on the toxicities of the ILs.

The current IL toxicity classifications are based on mass, not molar, concentrations. Therefore, the $EC_{50}$ values are presented in FIG. 2A, based on the mass. The ILs in this study were moderately toxic (decanoates and isostearates between 1-100 mg/L) or practically harmless (neodecanoates 100-1000 mg/L) according to their $EC_{50}$ values. Two $EC_{50}$ values, after 5 and 15 minutes incubation, are provided for reference purposes, since either of these incubation times is typically used in prior art utilizing *V. fischeri* bacteria. The toxic effect is time-dependent, particularly with relatively short incubation times (minutes time-scale). When the incubation time is increased, lower concentration is needed to achieve the median effect. Therefore 15-minute incubation results in higher toxicity (i.e. lower $EC_{50}$ value).

Since the aim of the study was to investigate if the IL toxic properties are caused by the permeation of the IL into the lipid bilayer, the number of molecules potentially interacting with the bacteria is of more interest. The toxicities were normalized to the number of the molecules in the solution and, therefore, presented in FIG. 2B and in Table 1 as molar concentrations.

Figure 1:
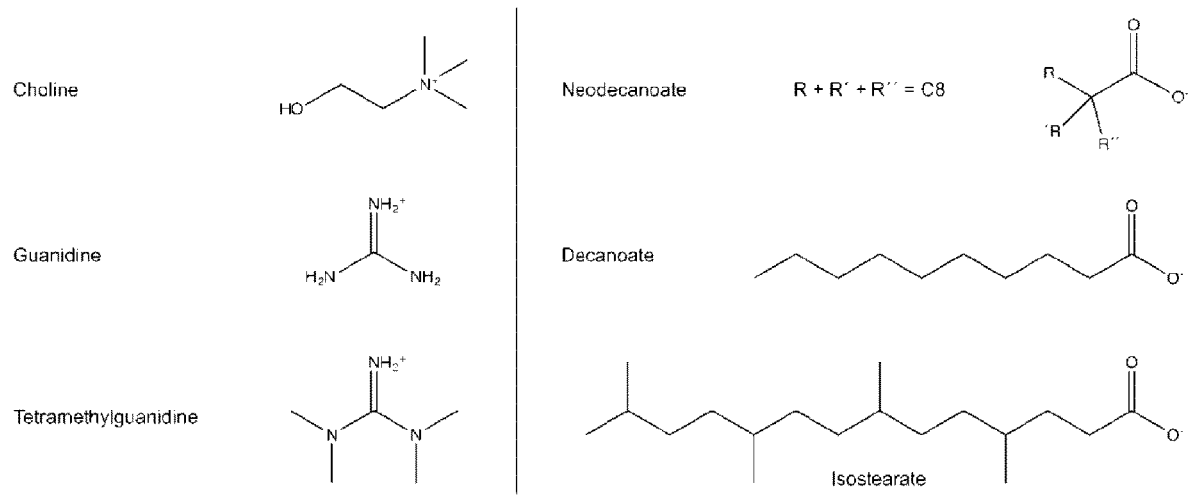
FIG. 1 shows structures of the IL cations and anions. The structures of neodecanoate and isostearate are suggestive, since detailed structural analysis is yet to be performed.
Figures 2A, 2B:
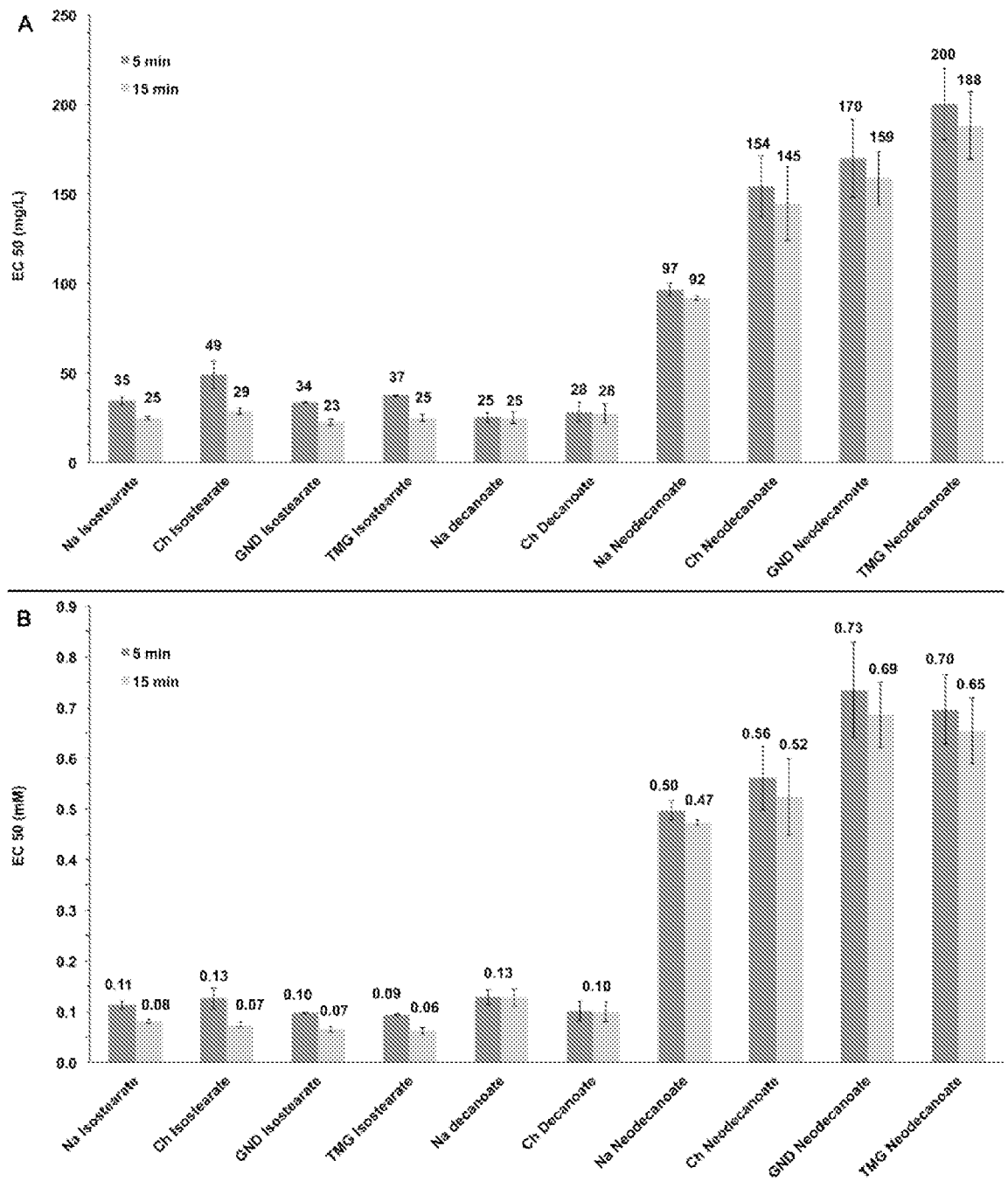
FIGS. 2A and 2B show the EC50 values defined for the ILs using *Vibrio fischeri* bacteria with 5 min and 15 min incubation. Presented as mass (FIG. 2A) and as molar (FIG. 2B) concentrations.

It is known that longer alkyl chains increase the toxicity of ILs. Therefore, merely based on chain lengths, the Na and Ch isostearates should be significantly more toxic than the corresponding decanoates (FIG. 2B). The similar toxicity of these isostearates and decanoates suggest that branching of the isostearates remarkably decreases their toxicity. Unfortunately, the comparison with corresponding stearates could not be performed due to their extremely poor water solubility. The difference between the $EC_{50}$ values of Na and Ch decanoates and corresponding neodecanoates evidently illustrate the effect of the branching on the toxicity: straight-chain decanoates are more toxic than the branched neodecanoates (average values ~0.1 mM vs. ~0.5 mM, see FIG. 2B for comparison).

Since the toxicity measurements were performed in 2% NaCl aqueous solution, subtle changes in the Na-cation concentrations did not affect the viability of the cells. Therefore, the choline cation did not have any practical effect on the toxicity of any of the Ch containing ILs: Ch isostearate and Ch neodecanoate are somewhat less toxic than their Na-cation-containing equivalents, whereas, Ch decanoate is more toxic than Na decanoate (FIG. 2B). However, taking into account the standard deviations the differences are insignificant.

The GND and TMG isostearates have similar toxicities and appear to be somewhat more toxic than their Na and Ch equivalents (FIG. 2B). In contrast, within the neodecanoate group GND and TMG are evidently less toxic than their Na and Ch equivalents.

In summary, the length of the anion acyl chains seems to have a strong correlation on the toxicity of the ILs in this study. Similar effect has been observed before with differing ILs and test organisms. Increase in the anion alkyl chains of phosphonium-carboxylate ILs (C6, C10, C14, C16 and C18) has increased the IL toxicity (measured using Chinese hamster ovary cell culture) as far as the molecules are dissolved as singly dispersed molecules. Another study showed that the increase in choline-carboxylate-IL toxicities follow the alkyl chain length (C2<C3<C4<C5<C6<C8<C10). Similar effect was also observed with choline-carboxylate ILs with C2-C10 using HeLa and SK-MEL28 cells (keratinocytes)—however, the trend was not linear. Particularly, with shorter chains (<C6) there were large variations between the effects induced by the differing chain lengths. According to one study, the toxicity of choline carboxylates measured with MCF-7 (human breast cancer cell line) was actually slightly decreasing, as a function of the alkyl chain length (C2-C4 and C6). It seems that the length of the acyl chain mostly increases the toxicity with alkyl chain lengths >6 carbons, whereas, with shorter chains the effects are not as predictable and may be more affected by the cation.

In the present study, branching of the anion alkyl chain decreased toxicity. In general, the effect of branching, however, is not as straightforward and seems to be greatly dependent on the core ion of the surface-active component.

Overall, in the present study the effect of the cation was small compared to the effect of the anion. Such an effect has also been detected in other studies, for instance, for choline carboxylates. In the present study, the cation affected the $EC_{50}$ values only within the neodecanoate analogues: surprisingly, GND and TMG cations decreased the toxicity of the ILs when compared to their Na and Ch equivalents.

Differential Scanning Calorimetry

The aim of the DSC study was to investigate if there is a connection between the $EC_{50}$ values defined with *V. fischeri* bacteria and the rupture point (or range) of the model lipid layer (DPPC). The ILs in the present study, and particularly their anionic components, are surface-active molecules. They are expected to permeate into DPPC liposome bilayers used as biomimetic membranes. This will result as a decrease in the order of the DPPC bilayers and consequent gradual transformation of the bilayer into a more fluidic phase, such as the ones formed by unsaturated phospholipids at room temperature.

Since the $T_m$ of pure DPPC layers is well established (approximately 41.3° C.) and very repeatable, DPPC was chosen as the reference biomimetic membrane. This transition takes place when the lipid bilayer undergoes a transition from ordered gel phase into a fluidic L-alpha phase. The phase transition of a lipid bilayer (such as DPPC) is a cooperative phenomenon, i.e. conformational change in one molecule forces adjacent molecules to adapt due to the high ordering of the bilayer. Therefore, phase transitions of bilayers made of pure lipids take place during a very narrow temperature range and results in sharp endothermic peaks. In contrast, impurities such as other surfactants mixed with the phospholipids decrease the ordering of the bilayers. This decreases cooperativity of the lipids and results in wider peaks.

When surface-active molecules interact with or permeate into a lipid layer, the $T_m$ starts to drift gradually towards lower temperatures, as a function of the surface-active molecular concentration. This is due to the decreased order of the lipids in the condensed gel-phase membrane. Due to the interaction of surfactants and liposomes, it is possible that new organized surfactant-lipid vesicles are formed. At least two differing scenarios are possible: i) The surfactants mixed with lipids disturb the organization of the lipid layer and the endotherm peak, caused by the transition, disappears gradually as the proportion of the surfactant increases. ii) The surfactant and the lipids form a new fairly organized bilayer and formation of new phases is plausible. When the amount of the IL components in the bilayer grows high enough, the newly formed vesicle may also rupture (applies for both scenarios).

The mechanism of the rupture may be similar to what has been observed for neutral, anionic, and cationic surfactants and model lipid bilayers. First the surface-active IL components permeate into the DPPC bilayer and IL/DPPC vesicles are formed (IL monomers+DPPC liposomes=IL/DPPC vesicles). At this phase an endotherm produced by the main phase transition is observed, but at a different $T_m$ than for the pure lipid layer. The permeation of the surfactant takes place until the membrane is saturated with the surfactant. When the concentration of the surfactant is increased beyond a certain IL- and/or lipid-dependent threshold, it is plausible that the bilayer gradually disintegrates and additional IL/DPPC aggregates are formed. Therefore, possibly a state is reached in which aggregates coexist with the remaining IL/DPPC vesicles. However, the aggregates may not possess such an organized structure that any phase transitions would take place. Endotherm would only be produced by the transition originating from the remaining IL/DPPC bilayers. When the concentration of the surfactant is further increased, the IL/DPPC vesicles rupture and remain as IL/DPPC aggregates.

The DSC experiments were performed in order to find out the IL concentrations that induce the drift in the DPPC bilayer phase transition temperature. FIG. 3 illustrates the representative endotherms, which were recorded during the second heating scans. Since the heating and the cooling scans were performed three times, the second heating endotherm was selected as the representative one. Often the first endotherm differed from the two latter ones, which mostly were identical to each other. If the baseline variations observed during the first heating scans were not observed on the following two scans and with other concentrations of the same ILs, they were regarded as artefacts. With certain ILs, the intensity of the peaks were decreasing with the heating scan. Slight drifting of the peaks was also observed. These changes are most likely due to reorganization of the IL-lipid membranes as the system is heated up and cooled down. The difference observed particularly between the first and the second heating scans is explained by the fact that; when the DPPC lipid layer is heated to a fluidic state, the IL components can more easily permeate into the lipid layer and the system equilibrates. During the cooling and a second heating scan the surface active impurities are already within the layer and therefore, less change is observed between two latter scans. Cooling scans (not shown) were recorded in order to follow the stability of the system, however, no further analysis of the cooling scans was performed. Such heating and cooling scans are standard in DSC experiments.

Typically, in toxicity measurements the defined $EC_{50}$ values are normalized based on the number of individual organisms used for the experiments (number of cells), and therefore the ratio between the number of bacteria and the concentration of the toxicant does not affect the $EC_{50}$ value. In contrast, the concentration of the IL generating an observable impact on the bilayer phase transition (effective concentration) is dependent, not only on the concentration and properties of the ILs, but also on the concentration of the liposomes (molar concentration of lipid). The effect is dependent on the ratio of these two components. Therefore, the effective concentrations of the ILs were not expected to be similar to the $EC_{50}$ values. The 0.4 mM lipid concentration was chosen since it gives a symmetrically shaped and repeatable signal with the calorimeter that we used.

The DSC results are discussed in more detail in the following text for each IL carboxylate group. The concentration range within which the phase transition endotherm was lost is presented in Table 1. Instead of referring to the peak areas, which define the energy taken by the transition (cal/° C./mol), corresponding peak heights are referred to in the text, since the relative changes in the peak heights are more easily observed by visual inspection.

Isostearates

Figure 3A:
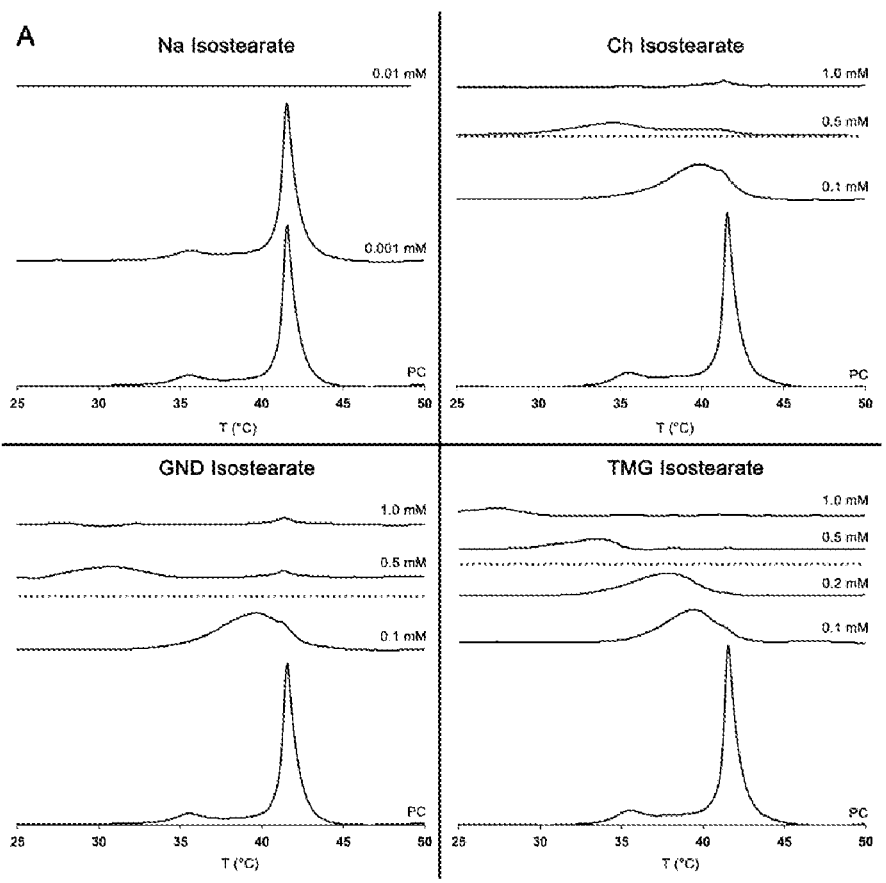
FIGS. 3A and 3B show endotherms measured for pure DPPC and mixtures of DPPC (0.4 mM) and differing concentrations of isostearates (FIG. 3A), decanoates and neodecanoates IL (FIG. 3B). The broken lines (where applicable) designate the limit after which the ILs are dispersed as aggregates (CMC).

The behavior of Ch, GND, and TMG isostearates were very similar and largely independent of the cation (FIG. 3A). Already 0.1 mM concentrations caused the transitions to considerably shift to lower temperature and the peak lost its sharp profile, suggesting that the order and cooperativity within the bilayer was remarkably decreased. At 0.5 mM the transitions shifted to ~35° C. and below, depending on the IL, and the peak height further decreased from the previous concentrations. The peaks caused by the main phase transitions were not detected anymore at 1.0 mM concentrations—a faint broad peak was still only barely visible for TMG isostearate.

Interestingly, a faint peak at the original DPPC transition temperature remained throughout the concentration range, particularly noticeable in Ch and GND isostearate endotherms. For GND isostearate 5, 10, and 20 mM concentrations were also measured (not shown in FIG. 3A) and the small peak was still observable in all of these endotherms, similar to the 0.5 and 1.0 mM concentrations. With TMG a barely detectable signal was observed, in the first heating scan endotherm but the peak was not visible in the second and third scans. In all of these experiments the intensity of these small peaks decreased approximately 2-4 fold between the first and second heating scans. It seems that for some reason, either a small amount of DPPC liposomes remain unaffected in the solution or phase separated regions remain in the IL/DPPC vesicles.

The behavior of Na isostearate deviated substantially from the other isostearates since the loss of the main phase transition, probably caused by the rupture of the bilayer, takes place already between 0.01 and 0.001 mM concentration. This suggests that the cation has also an impact on the IL-liposome interactions, with isostearates considerably decreasing the harmful effect.

Decanoates

Figure 3B:
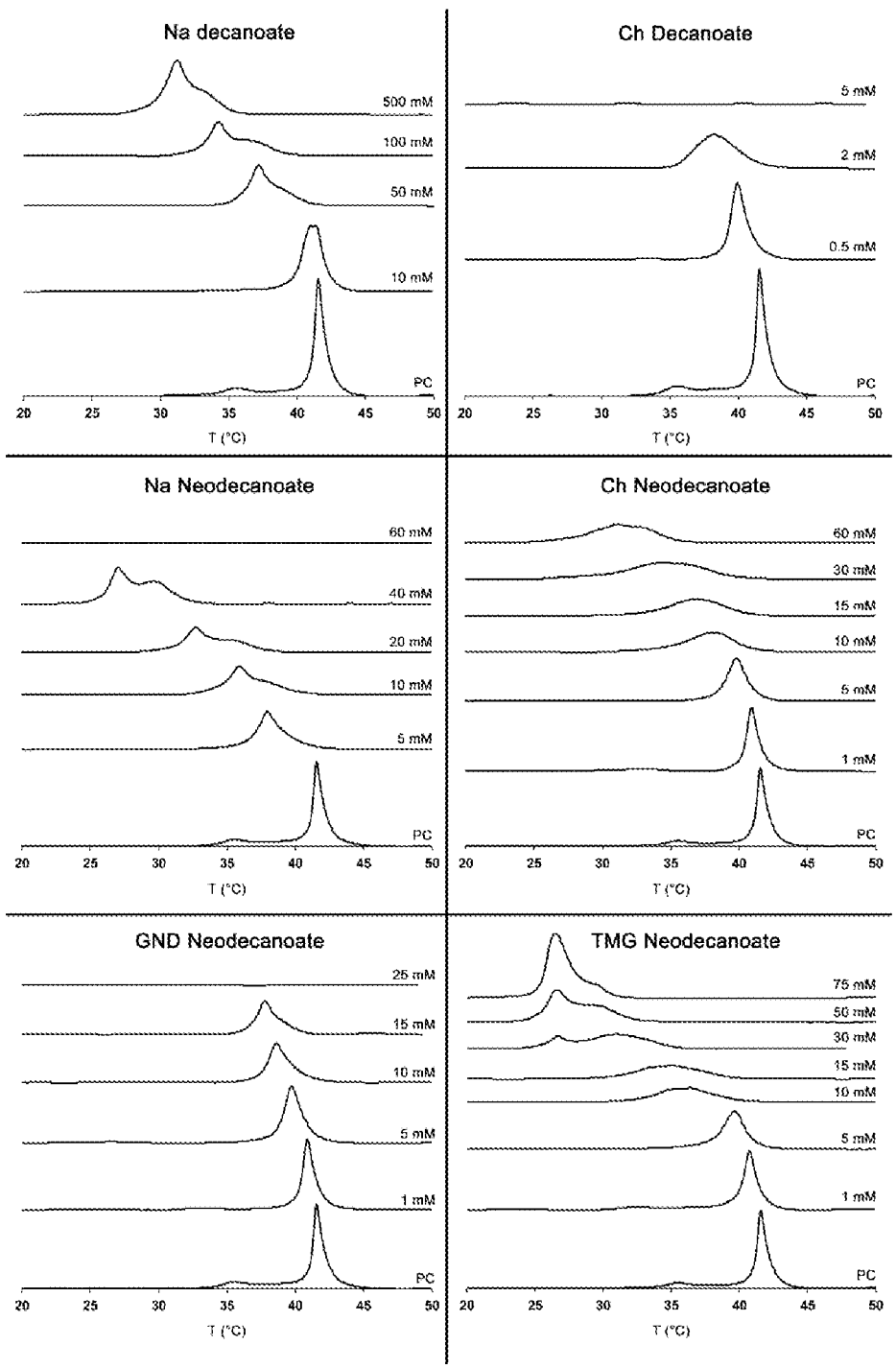

The decanoates, having very similar $EC_{50}$ values as the isostearates, show somewhat differing behavior in the DSC measurements (FIG. 3B). The changes in the $T_m$ behavior caused by Na decanoate permeation took place at considerably higher IL concentrations, than with isostearates. At 10 mM the shift was visible, as designated by the double peak. At 50 mM the $T_m$ was still above 35° C., but the peak height had decreased considerably. At 100 mM the peak height further decreased and another transition appeared at somewhat higher temperature (overlapping with the original transition). At 500 mM the transition further shifted to lower temperature. Instead of decreasing, the intensity of the original peak increased and also the second transition became more prominent. These observations suggest that new mixed IL-lipid vesicles are formed and that their bilayer can adapt a somewhat organized phase, when a certain IL-lipid proportion is reached. However, detailed phase transition behavior of these newly formed vesicles is not in the scope of this study. In contrast, the transitions in the Ch decanoate case were affected by remarkably lower concentrations and the loss of the transition took place between 2 to 5 mM concentration, possibly due to the rupture of the vesicle. Based on comparison between Na and Ch decanoates, the presence of the choline cation remarkably modifies the effect of the decanoate anion.

The effect of the Ch nonanoate (C9) on DPPC liposomes has been investigated by using DSC. Surprisingly, the effective concentrations were remarkably larger than the ones observed here with Ch decanoate. The concentration was increased up to 50 mM and a peak for the $T_m$ was still observed, whereas the endotherm was lost between 2 and 5 mM concentration using Ch decanoate in the present study.

Neodecanoates

The behavior of Na neodecanoate is similar to that of Na decanoate, however, at considerably lower IL concentrations (FIG. 3B). Formation of another transition is visible at 10 mM concentration and is more visible at 20 mM and 40 mM concentrations. In contrast to Na decanoate, the phase transition was lost between 40 mM and 60 mM concentrations most likely due to the rupture of the liposome. Ch and GND neodecanoates showed a more predictable behavior. For Ch neodecanoate a faint broad peak caused by the transition was observed until 60 mM concentration. Since no significant change in the height of the peak was observed after 10 mM concentration, no higher concentrations were measured. GND neodecanoate showed very predictable and consistent behavior until the rupture of the vesicle between 15 and 25 mM concentration.

TMG neodecanoate showed very similar behavior to GND neodecanoate until a concentration of 5 mM. At 15 mM, only a very faint broad peak was observed. Increasing the concentration even further, up to 30 mM, resulted in another transition. This transition was observed at a lower transition temperature than the main transition, in contrast to Na decanoate and Na neodecanoate. The intensity of this peak increased with increasing concentration, outgrowing the intensity of the original transition. 75 mM pure TMG neodecanoate was also measured as a reference and only a very minor signal (not shown) barely deviating from the baseline was observed, at approximately the same transition temperature as the largest peak in the 75 mM IL/DPPC experiment. This data also suggests that a new phase is formed when a certain IL/lipid proportion is reached, within the vesicle bilayer. This is supported by the results obtained with fatty acid/DPPC vesicles, by changing the fatty acid proportion within the bilayer. A similar formation of new endothermic peaks, below the $T_m$, was detected with oleic acid. According to the authors, these are caused by formation of coexisting phases in the vesicles.

Critical Micelle Concentrations

The critical micelle concentrations were measured in order to define the concentration threshold for aggregation of singly dispersed IL molecules (micelle formation). The ILs may interact differently with liposomes depending on whether they are occurring as singly dispersed molecules (monomers) or as aggregates. Since the IL anions in this study are surface-active isostearates, decanoates, and neodecanoates, the anion is expected to mainly define the CMC of the IL.

CMCs for the ILs are presented in Table 1.

that the presence of the cation does not remarkably affect their CMCs. CMCs for the decanoates are practically the same, 22±3 mM for Na and 23±4 mM for Ch decanoate and therefore the effect of the cation is miniscule. This is in line with a previous study,[6] but interestingly the value of 75 mM is somewhat higher than those defined here. For neodecanoates, the average values are notably higher—roughly between 100 and 450 mM. The cation seems to affect the CMCs of the branched isostearates and the neodecanoates. However, the effect is IL-dependent.

The Effect of CMCs on $EC_{50}$ Values and Ionic Liquid-Liposome Interactions

At $EC_{50}$ all the ILs are dissolved as monomers ($EC_{50}$<CMCs, see Table 1). For isostearates the CMCs are roughly in the same order of magnitude as the $EC_{50}$ values, whereas, for decanoates and neodecanoates the CMCs are considerably higher.

In DSC experiments the effective IL concentrations were closer to the CMCs and this had more impact on the analysis of the results. With Ch, GND, and TMG isostearate, the effective concentrations are very close to the CMC values

TABLE 1

The properties measured for the ILs: the EC50 values were determined using *Vibrio Fischeri* bacteria with 5 min and 15 min incubation; the concentration range within which the phase transition was no longer detected (Loss of transition); the critical micelle concentration (CMC) and the fitting method used for the CMC determination (superscript).

| Ionic liquid | M (g/mol) | EC50$_{5\,min}$ (mM) | EC50$_{15\,min}$ (mM) | Loss of transition (mM) | CMC (mM) |
|---|---|---|---|---|---|
| Na Isostearate | 306.47 | 0.11 ± 0.01 | 0.081 ± 0.004 | 0.001-0.01 | 0.72 ± 0.06[L] |
| Ch Isostearate | 387.65 | 0.13 ± 0.02 | 0.074 ± 0.005 | 0.5-1.0 | 0.50 ± 0.06[L] |
| GND Isostearate | 343.56 | 0.098 ± 0.002 | 0.066 ± 0.005 | 0.5-1.0 | 0.31 ± 0.08[S] |
| TMG Isostearate | 399.66 | 0.094 ± 0.001 | 0.062 ± 0.005 | 0.5-1.0 | 0.30 ± 0.04[S] |
| Na decanoate | 194.24 | 0.13 ± 0.02 | 0.13 ± 0.02 | — | 22 ± 3[L] |
| Ch Decanoate | 275.43 | 0.10 ± 0.02 | 0.10 ± 0.02 | 2.0-5.0 | 23 ± 4[L] |
| Na Neodecanoate | 194.24 | 0.50 ± 0.02 | 0.473 ± 0.006 | 40-60 | 422 ± 38[L] |
| Ch Neodecanoate | 275.43 | 0.56 ± 0.06 | 0.52 ± 0.08 | — | 319 ± 13[L] |
| GND Neodecanoate | 231.34 | 0.73 ± 0.09 | 0.69 ± 0.07 | 15.0-25.0 | 118 ± 2[L] |
| TMG Neodecanoate | 287.45 | 0.70 ± 0.07 | 0.65 ± 0.07 | — | 261 ± 11[L] |

[L]logarithmic fitting
[S]Sigmoidal fitting

As expected, for long-chain isostearates, CMCs are lower than for shorter-chain decanoates. Also, branching of the neodecanoates increases the CMC. FIG. 4 exemplifies three differing curves used for defining the CMCs of Ch isostearate, decanoate, and neodecanoate. For Ch isostearate, a distinct breaking point is noticeable at a concentration of ~0.5 mM. For such cases, linear, sigmoidal and logarithmic fits give very similar results independent of the fitting method. For Ch decanoate, the slope is milder and the determination of a specific point for the CMC is more difficult. For such ILs the logarithm of the IL concentration and logarithmic fit was utilized since more precise values can be obtained with this method. For Ch neodecanoate, the slope is even milder than for decanoate. Aggregates and singly dispersed molecules co-exist over a wide concentration range. Based on the graphs of Ch decanoate and neodecanoate, the aggregation begins at low concentrations. The fitting method used for each IL is designated in Table 1. A logarithmic fitting was used for all ILs, except for GND and TMG isostearate for which a sigmoidal fitting was utilized.

Among the isostearates, the average CMC values are in the same order of magnitude, 0.3-0.7 mM, demonstrating (Table 1). For Ch, GND, and TMG isostearate an endotherm is observed at concentrations just below the CMC (at 0.1 mM for Ch, GND and at 0.2 mM for TMG isostearate). However, the endotherm is barely visible above the CMCs and at 1 mM no peak is visible. Further, endotherms for 2 mM Ch, GND, and TMG isostearates were measured but no endotherms were observed (thermograms not shown). Based on this data, the impact of the ILs is very similar, independent of the aggregation, since no visible change in the effect is detected even though the CMC is exceeded. There are at least two possible explanations for these observations.

i) One possible mechanism for such behavior is presented in the following; When the IL concentration in a mixture of ILs and DPPC liposomes is below the CMC, the free surface-active IL monomers permeate into the DPPC bilayer and most likely remain there. When the concentrations of the ILs and lipids are in the same order of magnitude (as with isostearates), a state is reached where all the IL monomers are incorporated into the bilayer and none exist free in the solution. Alternatively, the bilayer is saturated with the ILs, the monomers stop permeating into the bilayer, and a certain concentration of monomers remain in the solution. This is very likely when the concentration of the IL greatly exceeds the concentration of the lipids. In contrast, above the CMC there is a coexistence of IL monomers and IL aggregates. At and above the CMC the concentration of the monomers equals the CMC and all the monomers above this concentration are included in aggregates. Similar to the description above, free monomers can still permeate into the liposomes. Since the concentration of free IL monomers in the solution is decreasing, IL aggregates gradually disintegrate into free monomers due to the dynamic equilibrium existing between free monomers and aggregates. This aggregate disintegration process takes place until the concentration of the monomers again equals the CMC, or when there are no IL aggregates remaining. Therefore, with this mechanism the apparent impact of aggregated ILs can be similar to that of free monomers.

ii) Another possible explanation is the effect of temperature on the CMCs. The CMCs of anionic surfactants are known to increase somewhat as a function of temperature. Therefore, a similar effect could also be caused by an increase in the CMCs during the heating scans. First, when the CMC is exceeded at lower temperature (e.g. at room temperature), the ILs form aggregates. When the temperature is raised during the heating scans, the aggregates disintegrate into monomers due to the consequential raise in the CMC. Therefore, more free monomers are available to interact with the DPPC liposomes.

For Na isostearate the CMC is clearly higher than the concentration where the phase transition peak is lost. At such a concentration singly dispersed IL molecules interact with the liposomes. The loss of the peak is caused either by formation of a new fluidic IL-lipid phase or by rupture of the membrane.

The IL concentration range in the DSC measurements was clearly below the CMCs for the decanoates and neodecanoates, except for sodium neodecanoate, which was used as a reference for the ILs. Therefore, except for sodium neodecanoate, the data clearly shows that singly dispersed IL molecules interact with the liposomes. A thermogram was measured for pure 50 mM sodium decanoate and no signal was observed. This suggests that the transition actually results from the decanoate/DPPC liposomes and not from a possible phase transition taking place in the IL aggregate.

Seven Ch-, GND-, and TMG-based ILs with long chain anions were investigated. The toxicities were defined mainly by the long chain anions—the longer the chain, the more toxic the compound. Such impact has been seen before with ILs with long chain cations and anions. The branching of the anions decreased the toxicities of the ILs. The cations did not have a significant impact on the toxicities of decananoates and isostearates, but the GND and TMG neodecanoates were surprisingly somewhat less toxic than their Ch equivalent.

DSC measurements were utilized to investigate the potential effect of the surface-active ILs on DPPC liposomes. These liposomes were used as biomimetic lipid bilayers and the $T_m$ of the membrane was followed as a function of the IL concentration. The chain length of the anion determined greatly the extent to which the ILs affected the liposomes, as well as the toxicities. The isostearates affected the liposomes at concentrations<1.0 mM, Ch decanoate at concentrations of 0.5-5 mM, and the neodecanoates at concentrations of >>1 mM. The presence of Ch, GND, or TMG cations evidently had an impact on the behavior of all the anions, when compared to the Na salts of each anion. There were no considerable differences between Ch, GND, and TMG isostearates, whereas, differing effects induced by the cations were observed for decanoates and neodecanoates. However, no trend was observed for the effect of the cations, moreover, the behavior was IL-dependent.

Based on this study, DSC is a valid tool for investigating the interactions between the surface-active ILs and biomimetic lipid layers. According to the present study tentative predictions of the toxicity of comparable (similar types of) ILs can be done. However, the toxic IL concentrations cannot be estimated. Considering bacterial cell walls or other biological membranes and the biomimetic DPPC liposomes, used in this study, two very different lipid layers are investigated. The DPPC forms highly organized bilayers below its $T_m$, whereas the bacterial cell walls, as well as other biological lipid bilayers, are fluid phase mixtures of several differing lipid species and proteins. Therefore, the fluid lipid layers are more susceptible for permeation of surface-active impurities than the condensed DPPC bilayers. Additionally, the $EC_{50}$ values are normalized to the number of bacteria, whereas the effective concentrations in the DSC measurements depend on the arbitrary selection of the lipid amount. Therefore, it cannot be expected that the $EC_{50}$ concentrations would match the effective concentrations used in the DSC measurements.

Also, the analysis of DSC results is dependent on what is considered to be a toxic concentration in the model membrane. A very small proportion of impurities permeating into the membranes of the model organism may be toxic. In contrast, a similar proportion of lipids in the biomimetic membranes may not have any considerable effect on the phase transition behavior. In this study the aim was to investigate large-scale effects such as the rupture of the liposomes. Therefore, the effective concentrations for the ILs are high compared to the $EC_{50}$ values, particularly for shorter chain decanoates and neodecanoates.

Consequently, it needs to be remembered that even though the toxicities of the ILs in this study depended on their surface-active properties, the damage that they cause by permeating into the model organism bilayer may not be structural in essence. Moreover, the ILs may interfere with the function of vital membrane-dependent cell signaling pathways by disturbing the subtle organization of lipids and proteins in the bilayer.

Experimental Methods

Following methods and chemicals has been used in the experiments disclosed in this application and relating to the present invention.

Chemicals and Reagents for Toxicity and Interaction Studies

DPPC was purchased from Avanti Polar Lipids (Alabaster, Ala., USA). The HPLC grade chloroform was acquired from WVR international (Leuven, Belgium). The bacteria and the chemicals for running the Microtox assay where purchased form Modern Water (New Castle, Del., USA) The ultrapure water used in the experiments was first distilled and then filtered, and deionized using Milli-Q device.

Synthesis of Ionic Liquids

All ILs were prepared by simple mixing of the reagents in presence or absence of solvents, i.e. the base with the respective acid in a 1:1 molar ratio. Some reagents required elevated temperature or solvents; i.e. NaOH (pellets) and (solid) decanoic acid were pre-dissolved in methanol. Crystalline guanidinium carbonate required reaction in methanol at 50° C. Methanol was removed after acid-base synthesis by rotary evaporation down to ~10 mbars. Rotary evaporation was also employed to remove water, where present. Neodecanoic acid (Versatic™ acid 10) was kindly provided by HEXION B.V. (Columbus, Ohio, USA). Isostearic acid was the brand Pristorine™ 3501 (Croda International Plc, Snaith, East Yorkshire, UK), derived from di/trimerisation and hydrogenation of tall oil fatty acid grades. Detailed characterization-assignment of functional groups was performed by $^1$H NMR (600 MHz) in $D_2O$ or DMSO-$d_6$. Karl-Fischer titration was used to monitor water contents to below 1 wt %. All structures were either glass, liquid or solid at room temperature. Differential scanning calorimetry (DSC) and thermogravimetric analysis (TGA) data will be presented in further publications.

Four procedures were used to synthesize the different cation classes of ionic liquid (choline, guanidnium, 1,1,3,3-tetramethylguanidinium or sodium):

Choline isostearate (example): Isostearic acid (317 g) was added in one portion to a commercial solution of choline hydroxide (45% wt. in methanol, 300 mL, 281 g) in a 1 L Erlenmeyer flask. The solution was mixed at room temperature, upon which a mild exotherm was observed. Mixing was continued for a further 30 min. The product was then rotary evaporated in batches to remove methanol. A soft gel was formed which was left in the flask to cool overnight. The dry fractions were combined and bottled the following day to give quantitative yield. NMR analysis showed only trace impurities (supplementary material).

Guanidinium isostearate (example): Isostearic acid (370 g) was added in one portion to a solution of guanidinium carbonate (117 g) in methanol (217 g), in a 1 L Erlenmeyer flask. This was mixed for 45 min at 50° C. until a clear solution was obtained. The product was dried by rotary evaporation in batches. A soft gel was formed which was left in the flask to cool overnight. The dry fractions were combined and bottled the following day to give quantitative yield. NMR analysis showed only trace impurities.

1,1,3,3-Tetramethylguanidinium isostearate (example): TMG (145 g) was added over the space of a few minutes to isostearic acid (355 g) in 1 L Erlenmeyer flask. A mild exotherm was observed. The mixture was left to cool down to produce a soft gel in quantitative yield. NMR analysis showed only trace impurities.

Sodium isostearate (example): Crushed sodium hydroxide pellets (1.22 g) were added over the space of a few minutes to isostearic acid (8.65 g) in methanol (12.5 g) in a 100 mL Erlenmeyer flask. A mild exotherm was observed. The mixture was left to cool down to produce a soft gel in quantitative yield. NMR analysis showed only trace impurities.

Preparation of Liposomes

A stock solution of DPPC was prepared by dissolving DPPC in chloroform. Required amount of the stock solution was transferred into a glass test tube and the chloroform was evaporated under airflow in order to form a thin film of DPPC on the walls of the tube. The air-dried lipid film was held under vacuum desiccator at least for 2 h to remove the residual solvent. The lipid was dispersed into water to obtain a 4.0 mM liposome stock. The dispersion was incubated in an ultrasonication water bath for 30 min at 60° C. facilitating the formation of multilamellar liposomes.

*Vibrio fischeri* Toxicity Assay

The toxicities of the ILs were defined by measuring their $EC_{50}$ values using *V. fischeri* bacteria and Microtox luminometer/thermostate apparatus (Modern Water, USA). The response measured in this assay is the decay of bioluminescence produced by the bacteria. In short, the bioluminescence was measured before the exposure on the potentially toxic compound to determine the baseline luminescence. Consequently, the bacteria were exposed on minimum four differing toxicant concentrations in 2% (w/v) NaCl solution and the decay in the luminescence was recorded. Based on the concentration-dependent decay the $EC_{50}$ value was defined. The toxicities were defined at set time intervals of 5 and 15 minutes. Two independent measurements were performed for each IL as duplicates.

Differential Scanning Calorimetry

DSC was utilized in observing the changes induced by the ILs in the organization of the lipid bilayers. Here DPPC was used because the $T_m$ of the bilayer is well recognized—approximately 41.3° C. Typically, when surface-active compounds permeate into the lipid layer, the transition temperature starts to shift with an increasing proportion of the compound in the lipid layer. There are two additional transitions observed for DPPC aqueous solutions; the subtransition at 21° C. and the pretransition at 36° C. However, the subtransition at 21° C. is visible only if the lipid is incubated below the transition temperature for several days. The transition at 36° C. is highly dependent on the heating rate and therefore may have somewhat differing values depending on the experimental setup.

DSC measurements were performed using a Perkin Elmer DSC-17 calorimeter. Aqueous stocks of DPPC liposome dispersion and IL solution were mixed resulting in a lipid concentration of 0.4 mM with varying concentration of IL. The samples were degassed under vacuum in order to avoid bubble formation during the sample loading and the heating/cooling scans. The mixtures were exposed to a heating scan starting from 15° C. and ending at 50° C. and subsequent cooling scan from 50° C. to 15° C. The heating/cooling scans were repeated three times for each sample. The temperature was allowed to stabilize for 30 min before each scan. The temperature ramp was 60° C./hour. The reference during the measurement was ultrapure water.

Critical Micelle Concentrations

The surface-active molecules (surfactants) dissolve in aqueous solutions as monomers to certain concentration threshold, after which they start to build up into differing aggregates. This concentration threshold is called critical micellar concentration (CMC). However, for many surfactants the CMC is moreover a concentration range, not a specific concentration point, and the width of the range depends greatly on the structure of the compound. In its simplest form the surfactants, such as fatty acids, form micelles, as the term critical micellar concentration suggests. Other surfactants such as phospholipids, however, form for instance liposomes, regardless, the term CMC is used. CMC and the form of the aggregates are dependent on the surfactant structure.

The optical pendant drop method using a contact angle meter (CAM 200, KSV Instruments, Espoo, Finland) was used for determining the CMCs. In short, a series of differing IL concentrations in water solution was investigated. A pendant-drop of a constant height was formed and the surface tension of the drop was determined based on the drop curvature by using a fitting method according to Young-Laplace equation. The surface tension was determined based on the curvature and plotted as a function of the IL concentration.

The surface tension of the drop decreases as a function of increasing surfactant concentration because the singly dispersed IL molecules diffuse and orientate at the air-water interface and therefore reduce the surface tension. When the concentration reaches the CMC, the singly dispersed molecules form aggregates and no additional molecules diffuse to the surface of the drop. Therefore no change in surface tension is observed.

The CMCs were determined based on the intersection point of two trend lines fitted based on the data. The surface tension was either plotted as a function of IL concentration or logarithm of the concentration and either sigmoidal or logarithmic fit, respectively, was used. The choice of method was dependent on which method provided the best fit.

Although certain embodiments and examples have been described in detail above, those having ordinary skill in the art will clearly understand that many modifications are possible in the embodiments and examples without departing from the teachings thereof. All such modifications are intended to be encompassed within the below claims of the invention.

The invention claimed is:

1. A hydrotropic composition comprising an ionic liquid which comprises:
   (i) at least one surface active cationic component, which is selected from the group consisting of cholinium, guanidinium, and tetramethylguanidinium, and
   (ii) a carboxylate anion which comprises neodecanoate.

2. The composition according to claim 1, wherein the surface active cationic component originates from an organic salt which is in a molten state at temperatures below 100° C.

3. The composition according to claim 1, wherein the neodecanoate anion is obtained through Reppe-Koch chemistry of add-catalysed hydrocarboxylation on octene isomers, derived from propene polymerisation.

4. The composition according to claim 1, wherein the composition has a median effective concentration EC50 value >100 mg/l, measured using *Vibrio fischeri* bacteria.

5. The composition according to claim 1, wherein the composition has a median effective concentration EC50 value) of 100-1000 mg/l.

6. The composition according to claim 1, wherein the composition has an average critical micelle concentration CMC >100 mM.

7. The composition according to claim 1 wherein the composition has hydrotropic properties between 20/80 to 90/10% (w/v) ratio of composition to water.

8. The hydrotropic composition of claim 1, wherein the surface active cationic component comprises cholinium.

9. The hydrotropic composition of claim 1, wherein the surface active cationic component comprises guanidinium.

10. The hydrotropic composition of claim 1, wherein the surface active cationic component comprises tetramethylguanidinium.

11. The hydrotropic composition of claim 1, which is in the form of a gel.

* * * * *